(12) United States Patent
Steffens et al.

(10) Patent No.: US 8,382,678 B2
(45) Date of Patent: Feb. 26, 2013

(54) DISPLAY OF TARGET CARDIAC FLOW BASED ON CARDIAC INDEX CALCULATION

(75) Inventors: Brian J. Steffens, Maple Grove, MN (US); Mark Salzwedel, Eden Prairie, MN (US); Mark G. Bearss, Minnetonka, MN (US); Keith D. Rohde, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1495 days.

(21) Appl. No.: 11/977,847

(22) Filed: Oct. 26, 2007

(65) Prior Publication Data
US 2008/0221465 A1    Sep. 11, 2008

Related U.S. Application Data

(60) Provisional application No. 60/905,747, filed on Mar. 8, 2007.

(51) Int. Cl.
*A61B 5/02* (2006.01)
(52) U.S. Cl. .......................... 600/504; 600/481
(58) Field of Classification Search .................. 600/481, 600/500–502, 504–507
See application file for complete search history.

(56) References Cited

U.S. PATENT DOCUMENTS

| | | | |
|---|---|---|---|
| 5,103,828 A | 4/1992 | Sramek | |
| 6,783,328 B2 | 8/2004 | Lucke et al. | |
| 6,918,887 B1 | 7/2005 | Gremel et al. | |
| 6,939,307 B1 * | 9/2005 | Dunlop | 600/504 |
| 7,022,099 B2 | 4/2006 | Litzie et al. | |
| 7,022,284 B2 | 4/2006 | Brian et al. | |
| 7,201,870 B2 | 4/2007 | Olsen et al. | |
| 2007/0083145 A1 * | 4/2007 | Murakami et al. | 604/6.09 |

OTHER PUBLICATIONS

Taylor et al., A Comparison of the Estimation of the Basal Cardiac Output form a Linear Formula and the "Cardiac Index" Valifity of the Cardiac Index, Jul. 27, 1951, pp. 209-216.

* cited by examiner

*Primary Examiner* — Patricia Mallari
*Assistant Examiner* — Michael D'Angelo

(57) ABSTRACT

User interfaces for medical perfusion systems that provide oxygenation, filtering, and recirculation of blood in connection with various medical procedures are provided. In particular, methods of displaying and communicating a desired target flow rate and cardiac index during cardiopulmonary bypass surgeries are provided.

8 Claims, 6 Drawing Sheets
(2 of 6 Drawing Sheet(s) Filed in Color)

DISPLAY OF TARGET CARDIAC FLOW BASED ON CARDIAC INDEX CALCULATION

CROSS-REFERENCE TO RELATED APPLICATION

The present application claims priority to U.S. Provisional Application No. 60/905,747, filed Mar. 8, 2007, the entire contents of which are incorporated herein by reference.

TECHNICAL FIELD

The present invention is directed to user interfaces for medical perfusion systems that provide oxygenation, filtering, and recirculation of blood in connection with various medical procedures. In particular, the present invention is directed to methods of displaying and communicating a desired target flow and cardiac index during cardiopulmonary bypass surgeries.

BACKGROUND

Cardiac index is a tool often used by healthcare providers such as perfusionists. Cardiac index is a cardiodynamic measure based on cardiac output, which is the amount of blood pumped by the heart per unit time, measured in liters per minute (l/min). The cardiac output can also be thought of as the amount of blood the heart pumps through the circulatory system in a minute. To provide the cardiac index, cardiac output is indexed to a patient's body size by dividing the cardiac output by the body surface area (BSA) of the patent. Thus, the cardiac index is typically provided as $(1/\min)/m^2$. There are several algorithms to calculate a patient's body surface area, such as DuBois, Boyd and infant algorithms, for example. Typically, these algorithms are provided in large tables in reference books that can be utilized by the appropriate health care provider. Target cardiac flow rates are typically calculated by perfusionists using a combination of a body surface area equation and desired cardiac index values.

SUMMARY

The present invention provides methods of displaying and communicating a desired cardiac index during cardiopulmonary bypass surgeries. Cardiac index is a calculated value based on a patient blood flow and body surface area calculation. The present invention also preferably provides indicators or indicia on a flow display to communicate a visual or tactile indication of a desired flow rate to achieve a desired cardiac index. The present invention automates the calculation of target flow and supplies the perfusionist with a real-time indication of actual cardiac index and a graphical indicator of target flow versus current cardiac flow. The present invention assists the user in achieving desired cardiac index during cardiopulmonary bypass. The combination of automated calculation, real-time display of actual cardiac index and display of target cardiac flow on a flow graph significantly simplifies the task of managing patient blood flow to achieve a desired cardiac index.

In an aspect of the present invention a method of graphically displaying target blood flow rate on a display screen of a user interface during cardiopulmonary bypass surgery is provided. The method comprises the steps of providing patient data including height, weight, and a desired cardiac index to the user interface, displaying a first graphical indicator of actual blood flow rate in real time on the display screen, calculating target blood flow rate with the user interface, wherein the target blood flow rate is at least partially based on the patient data, and displaying a second graphical indicator of the calculated target blood flow rate on the display screen.

In another aspect of the present invention, a user interface for graphically providing a target blood flow rate during cardiopulmonary bypass surgery is provided. The user interface comprises a display screen, a first graphical indicator of actual real time blood flow rate displayed on the display screen, a second graphical indicator of target blood flow rate displayed on the display screen, wherein the target blood flow rate is based on a desired cardiac index, and a numerical value of actual real time cardiac index displayed on the display screen.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of this application, illustrate several aspects of the invention and together with description of the embodiments serve to explain the principles of the invention. A brief description of the drawings is as follows.

DETAILED DESCRIPTION

Figure 1:
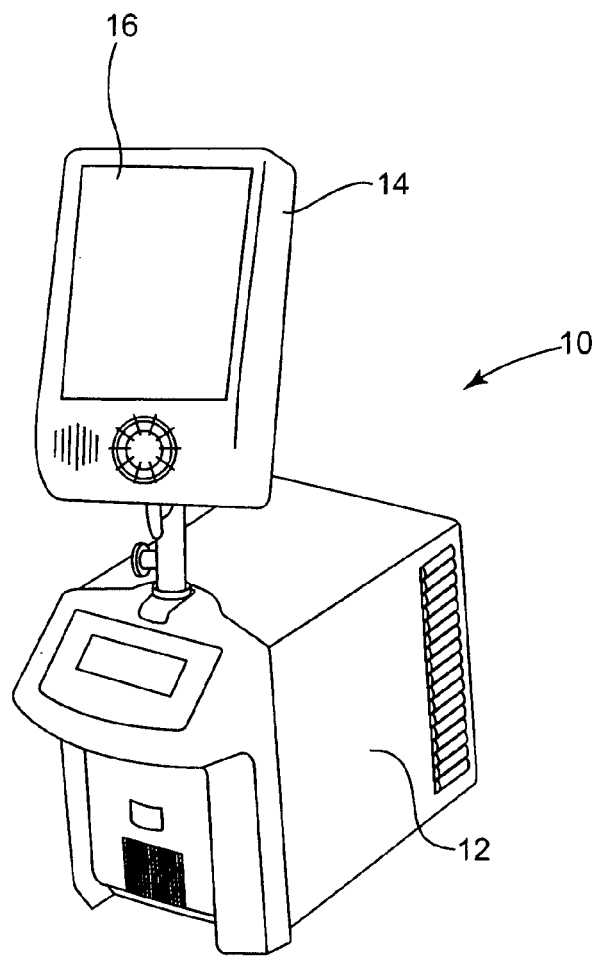
FIG. 1 is a perspective view of an exemplary pump console according to an aspect of the present invention showing a user interface and a base unit.
Figure 2:
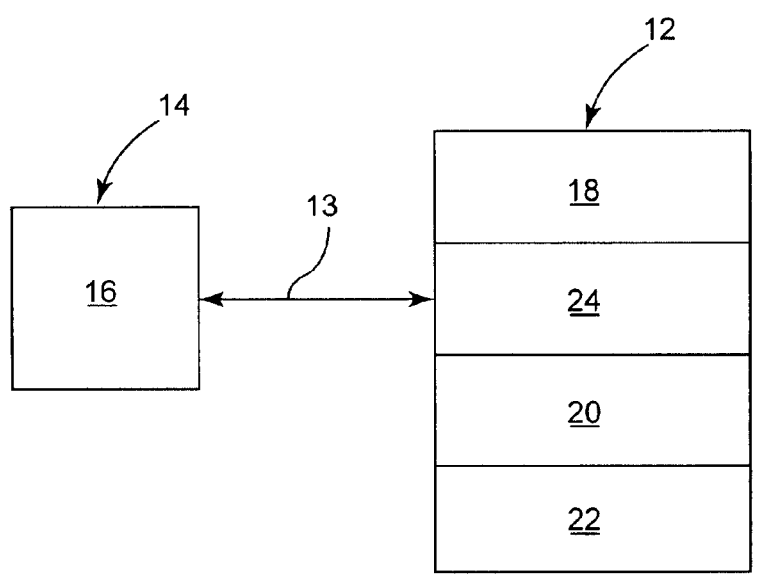
FIG. 2 is a schematic block diagram of the pump console of FIG. 1.

FIG. 1 is an exemplary perspective view and FIG. 2 is a schematic block diagram of a pump console 10 in accordance with the present invention. As shown, the pump console 10 comprises two primary components, including a base unit 12 and a user interface 14 that can communicate via communication link 13. The pump console 10 may comprise a stand-alone centrifugal pump control system or it may comprise an add-on module to commercially available heart-lung machines or blood pumps. The base unit 12 provides functionality for controlling pump speed, monitoring flow/pressure, battery backup, and providing communications to the user interface 14, for example. The user interface 14 includes a display 16 and user controls for operating and/or interfacing with the user interface 14. Display 16 preferably comprises a touch display/screen or other display device that allows input to be provided to an icon displayed on the screen by touching, contacting, or otherwise identifying the icon. Components of the base unit 12 and/or user interface 14 preferably comprise microcontrollers that provide communications through an asynchronous serial interface (RS232) or suitable communications protocol.

Figure 3:
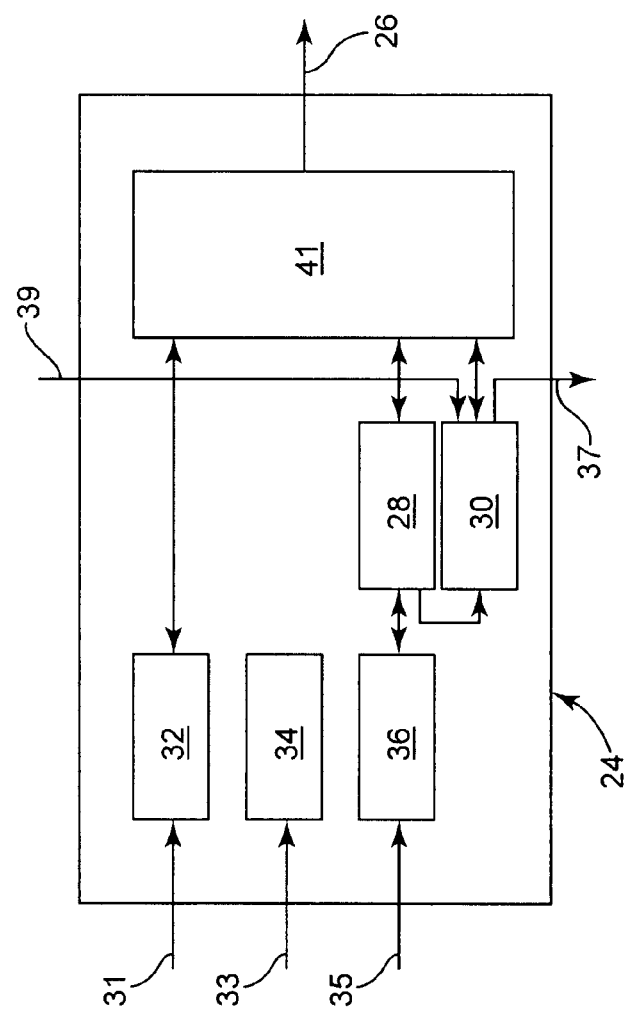
FIG. 3 is a schematic diagram of a safety module that can be used with the base unit according to an aspect of the present invention.

As illustrated, the base unit 12 comprises plural functional modules including a system controller module 18, motion/ pressure module 20, flow module 22, and safety module 24. The safety module 24 is schematically shown in further detail in FIG. 3 and preferably comprises a safety module bus interface 41, system bus interface 26, watchdog timer 28, and motor controller servo interface 30, which motor controller includes speed control input 39 and speed control output 37. The safety module 24 also preferably includes interfaces to safety systems such as a bubble detector interface 32, level sensor interface(s) 34, and an arterial clamp interface 36, which comprise inputs 31, 33, and 35, respectively. The bubble detector interface 32 provides an alarm to the operator when it detects the presence of bubbles or gross air in the tubing of the flow circuit. The level sensor interface(s) 34 provide an alarm or alert to the operator preferably based upon two separate level detectors placed on the patient blood reservoir. The arterial clamp interface 36 provides automated arterial line occlusion in the event of retrograde flow as determined by operator setup.

Figure 4:
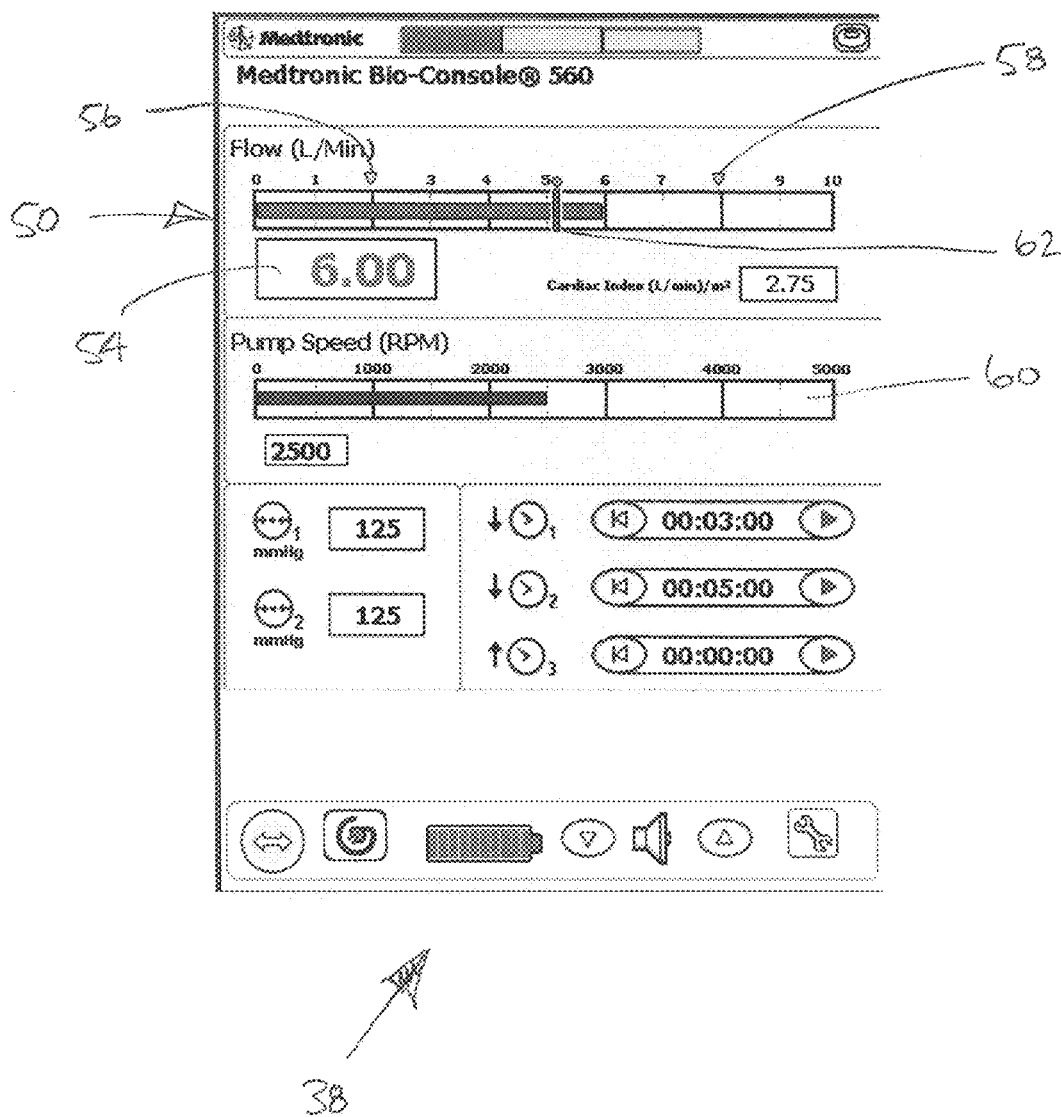
FIG. 4 is an exemplary main screen of a user interface in accordance with the present invention.

FIG. 4 illustrates an exemplary main screen 38 for the user interface 14 in accordance with the present invention. In use, main screen 38, as well as any other screen or screens of the user interface 14, are displayed on display 16 and are preferably capable of receiving touch inputs such as with a finger or appropriate stylus. Main screen 38 is preferably configured to display information related to operating parameters such as alert and alarm status, blood flow and pump speed, line pressure, user configurable timers, safety systems (if installed), and power status, for example.

Main screen 38 includes a flow display portion 50 that includes a flow gauge 52 that provides flow graphically, a first readout 54 that provides a numeric indication of blood flow, a low flow alert marker 56, a high flow alert marker 58, a second readout 60 that provides a numeric indication of cardiac index, and a target flow bar 62. The flow gauge 52, first readout 54, and second readout 60 each provide real time actual dynamic information regarding flow conditions. The low flow alert marker 56 and the high flow alert marker 58 are set by the user and trigger alarms that alert the user of the occurrence of low or high flow conditions. The target flow bar 62 represents the nominal rate of flow needed to achieve a desired cardiac index for a specific patient. It is displayed on the main screen 38 as a vertical green marker on the flow gauge 52.

Figure 5:
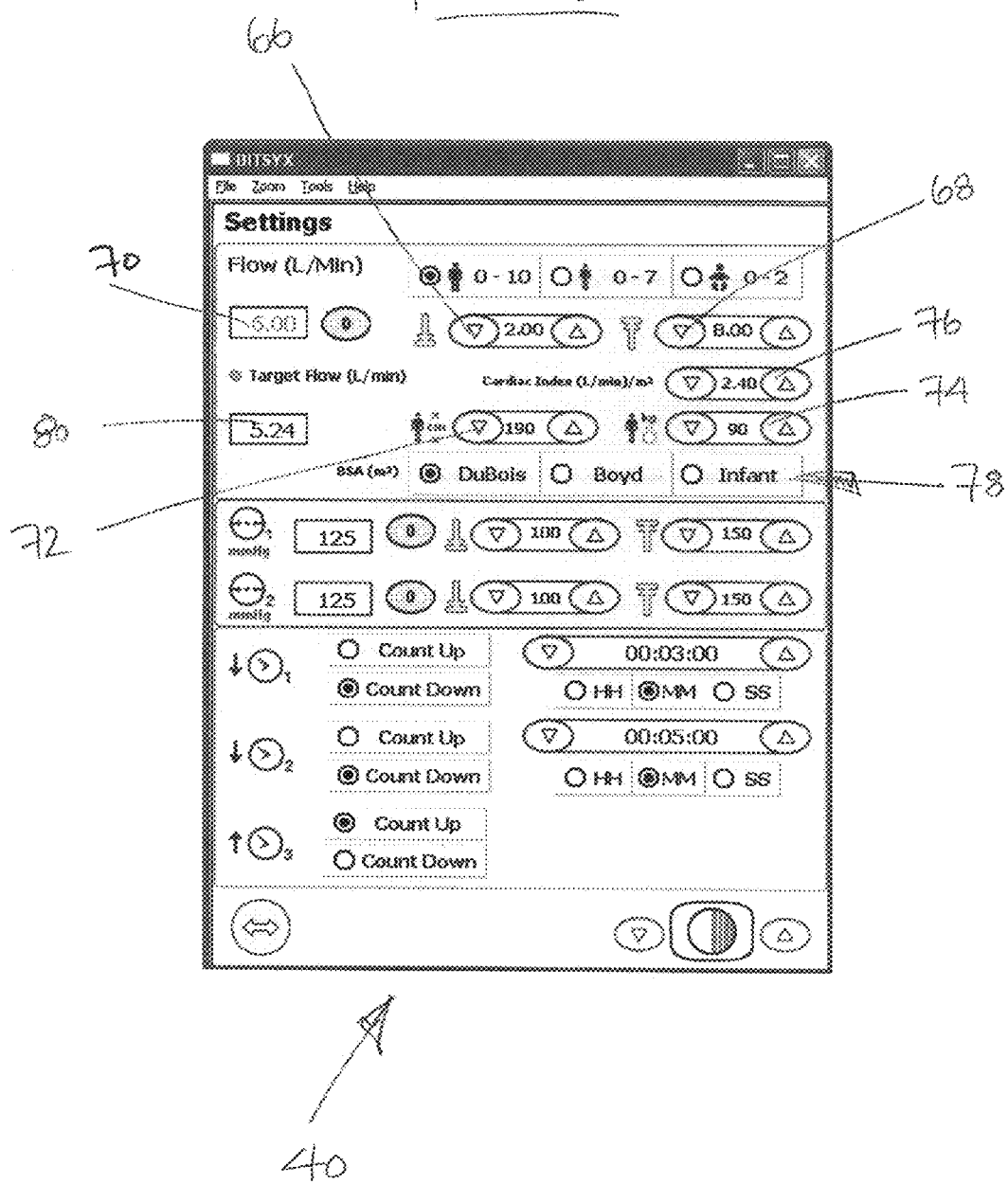
FIG. 5 is an exemplary settings screen of a user interface in accordance with the present invention.

In FIG. 5, an exemplary settings screen 40 is illustrated. Settings screen 40 provides the capability to set parameters such as blood flow range and upper/lower alert/alarm limits, target blood flow rate with cardiac index and height/weight calculator, pressure transducer zeroing and upper/lower alert/alarm limits, plural timer presets, and screen backlight intensity, for example. These settings can be adjusted by the operator by lightly touching or otherwise contacting a corresponding area on a screen. In many cases, this adjustment can be accomplished by contacting the up/down arrows associated with that particular parameter, for example. Settings screen 40 includes scale settings 64 for setting the scale of the flow gauge 52 of the main screen 38, a low flow setting 66 for setting the low flow alert marker 56 of the flow gauge 52, a high flow setting 68 for setting the high flow alert marker of the flow gauge 52, and a flow readout 70 that displays real time actual flow rate. Settings screen 40 also includes a body height setting 72, a body weight setting 74, a cardiac index setting 76, a body surface area algorithm setting 78, and a calculated target flow readout 80.

Figure 6:
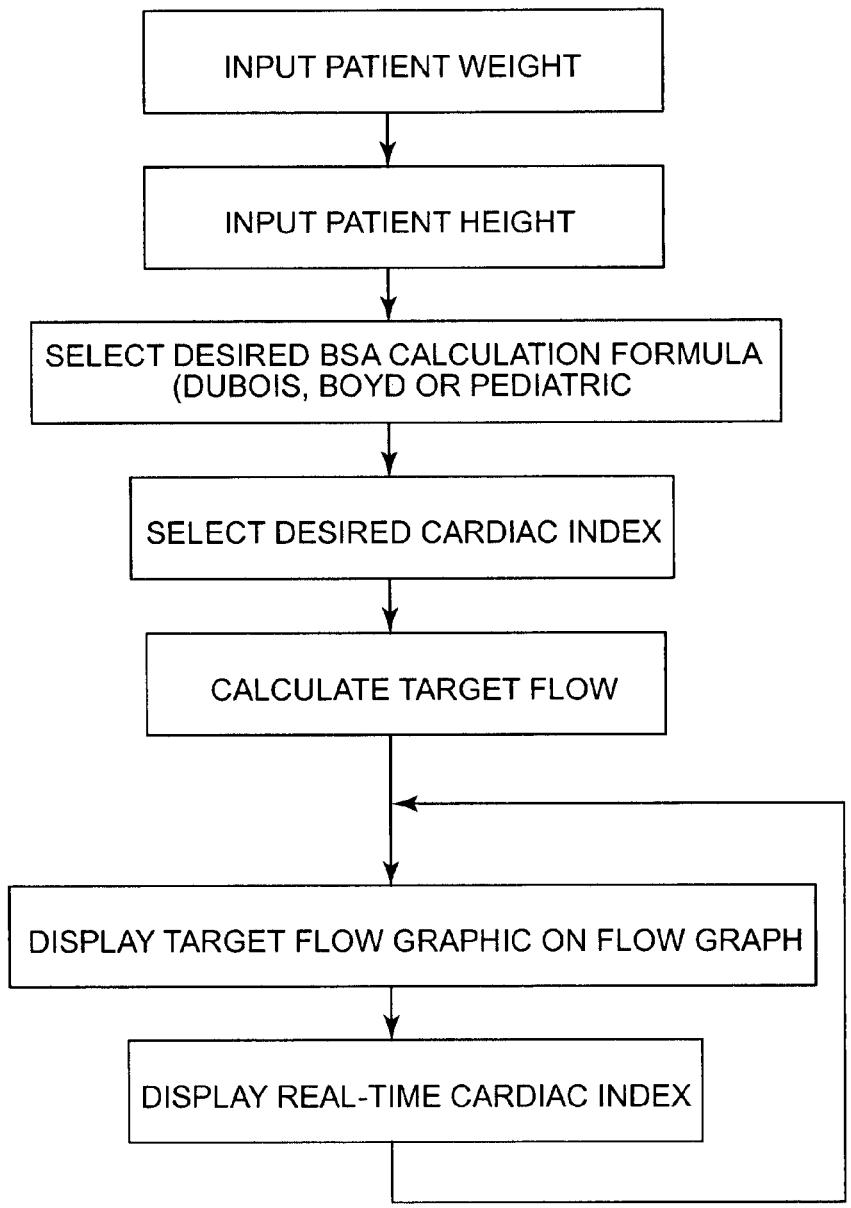
FIG. 6 is a flow chart showing an exemplary process for determining and displaying target flow in accordance with the present invention.

Settings screen 40 is used to calculate a target flow rate needed to achieve a desired cardiac index based on inputs entered into the settings screen 40. An exemplary process for calculating target flow is schematically illustrated in the flow chart of FIG. 6. Patient height, weight, and a desired cardiac index are entered onto the settings screen 40 by adjusting the corresponding settings. The user also selects the desired body surface area algorithm such as the DuBois algorithm, Boyd algorithm, infant algorithm or other known body surface area algorithms. The DuBois algorithm provides body surface area in square meters by taking $0.007184 \times \text{height (cm)}^{0.725} \times \text{weight (kg)}^{0.425}$. The Boyd algorithm provides body surface area in square meters by taking $0.0003207 \times \text{height (cm)}^{0.3} \times \text{weight (gm)}^{[0.7285-(0.0188 \times Log (gm))]}$. The infant algorithm provides body surface area in square meters by taking $0.024265 \times \text{height (cm)}^{0.3964} \times \text{weight (kg)}^{0.5378}$. The settings screen 40 then displays target flow at the target flow readout 80 on the settings screen. This same target flow is also displayed on main screen 38 as target flow bar 62, which is preferably a vertical green bar overlayed on the flow gauge 52 as illustrated. Although a green bar is described herein because the color green often signifies a "go" or positive situation, it is possible for the target flow bar 62 to be any desired color, where this color may optionally be selectable by the user. In any case, the color of the target flow bar 62 can be visually distinct from other surrounding colors on the main screen 38, or the color can be relatively similar to the colors of the items that are near to it. The present invention thus advantageously automates the calculation of target flow and provides the user with a real-time indication of actual cardiac index and a graphical indicator of target flow versus current cardiac flow. Such a display assists the user in achieving desired cardiac index during cardiopulmonary bypass because it eliminates hand calculation while providing a simple, real-time visual indicator of the target blood flow. The combination of automated calculation, real-time display of actual cardiac index and display of target cardiac flow on a flow graph significantly simplifies the task of managing patient blood flow to achieve a desired cardiac index.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of graphically displaying target blood flow rate on a display screen of a user interface during cardiopulmonary bypass surgery, the method comprising the steps of:
   providing patient data including height, weight, and a desired cardiac index to the user interface;
   displaying a first graphical indicator of actual blood flow rate in real time on the display screen;
   calculating target blood flow rate with a processing component associated with the user interface, wherein the target blood flow rate is at least partially based on the patient data; and
   displaying a second graphical indicator of the calculated target blood flow rate on the display screen.

2. The method of claim 1, further comprising displaying a numerical value of an actual cardiac index in real time on the display screen.

3. The method of claim 1, further comprising displaying a numerical value of actual blood flow rate in real time on the display screen.

4. The method of claim 1, wherein the step of displaying a second graphical indicator of the calculated target blood flow rate on the display screen comprises overlaying the second graphical on the first graphical indicator.

5. The method of claim 1, wherein the step of displaying a second graphical indicator of the calculated target blood flow rate on the display screen comprises displaying a vertical green bar on the display screen.

6. The method of claim 1, wherein the step of providing patient data to the user interface comprises displaying a settings screen and entering the patient data into the settings screen.

7. The method of claim 6, further comprising selecting a body surface area algorithm from the settings screen.

8. The method of claim 7, wherein the patient data further comprises the selected body surface algorithm.

* * * * *